United States Patent [19]

Flint et al.

[11] Patent Number: 4,528,028

[45] Date of Patent: Jul. 9, 1985

[54] USE OF CERTAIN HALOGEN-CONTAINING AMINO-ACID COMPOUNDS FOR CONTROLLING THE GROWTH OF UNWANTED PLANTS

[76] Inventors: Dennis H. Flint, 1316 Amy Ave., Modesto, Calif. 95355; Richard B. Silverman, 2921 W. Chase Ave., Chicago, Ill. 60645

[21] Appl. No.: 532,414

[22] Filed: Sep. 15, 1983

[51] Int. Cl.³ ............... A01N 37/02; A01N 37/06; A01N 37/18

[52] U.S. Cl. .................................... 71/113; 71/106; 71/118; 71/DIG. 1

[58] Field of Search .................... 71/113, 106, 118

[56] References Cited

U.S. PATENT DOCUMENTS 4,326,071 4/1982 Bey et al. ..................... 562/574
4,351,954 9/1982 Muramatsu et al. ............ 562/574

Primary Examiner—Catherine L. Mills

[57] ABSTRACT

Growth of unwanted plants is controlled by certain halogen-containing aminocarboxylic acid compounds.

2 Claims, No Drawings

USE OF CERTAIN HALOGEN-CONTAINING AMINO-ACID COMPOUNDS FOR CONTROLLING THE GROWTH OF UNWANTED PLANTS

DESCRIPTION OF THE INVENTION

It has been found that the growth of plants is adversely affected by halogen-containing aminocarboxylic acids, and derivatives thereof, of the formula:

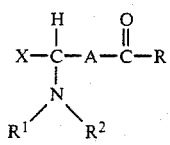

wherein X is (halogen)$CH_2$—, (halogen)$_2$CH—, or (halogen)$_3$C—; A is —$CH_2$—$CH_2$— or —CH=CH—; R is —OH, —$OR^3$, —$NH_2$ or —$NHR^3$, wherein $R^3$ is alkyl of one to six carbon atoms; $R^1$ is hydrogen, $R^2$ is hydrogen, —C(O)$R^4$, —C(O)$OR^4$ or —C(O)—$CH_2$—$OR^5$ wherein $R^4$ is alkyl of one to six carbon atoms optionally substituted by halogen, or is phenyl or benzyl optionally substituted by from one to three of one or more of halogen, nitro, hydroxyl and alkyl, alkoxy and alkylthio of from one to four carbon atoms, and $R^5$ is one of the phenyl moieties represented by $R^4$, or $R^1$ and $R^2$ together represent an alkylidene moiety

wherein $R^6$ is hydrogen and $R^7$ is a moiety represented by $R^4$, or $R^6$ and $R^7$ each is alkyl of from one to four carbon atoms, or is one of the phenyl moieties represented by $R^4$.

In these compounds, each alkyl moiety suitably is either straight-chain or branched-chain. The term "halogen" designates one of chlorine, bromine and fluorine.

Because of their phytotoxicity, a preferred subclass of the compounds of Formula I is composed of those compounds wherein X is $FCH_2$—, $R^1$ is hydrogen, $R^2$ is hydrogen, R is hydroxyl and A is —$CH_2$—$CH_2$—.

Salts of these compounds also are contemplated, suitable salts being those of alkali metals, alkaline earth metals, amines, and ammonia, and, where $R^1$ and $R^2$ both are hydrogen, the hydrohalide salts. Suitable amine salts include those of mono-, di- and tri-alkyl- and alkanolamines wherein each alkyl moiety contains up to 20 carbon atoms.

Since the carbon atom of the amino acid to which the amino moiety is bonded is a chiral center, the compounds can exist in the form of optical isomers, being in either the R— or S— absolute configuration. Preferably, they are in the S— configuration. Those compounds wherein A=—CH=CH— also can exist in the form of cis- and trans-(E—,Z—) configurations. The activities of the individual isomers with respect to plants may differ, and in the cases of the individual species of the compounds of Formula I whose preparation is described in the examples, hereinafter, the isomeric content of the products has not been ascertained. The invention contemplates all of the active isomers and mixtures containing them, both those which result from the method of synthesis, and those which have been created deliberately.

Compounds of Formula I wherein X is (halogen)$CH_2$—, A is —$CH_2$—$CH_2$—, R is hydroxyl, and both of $R^1$ and $R^2$ are hydrogen, are known compounds which can be prepared according to the method described by R. B. Silverman and M. A. Levy, Journal of Organic Chemistry, volume 45, pages 815-818 (1980). Compounds of Formula I wherein X is $FCH_2$—, $F_2CH$—, or $F_3C$—, A is —$CH_2$—$CH_2$—, R is hydroxyl, $R^1$ is hydrogen, and $R^2$ is hydrogen or acyl, and methods for their preparation are disclosed in U.S. Pat. No. 4,326,071. Corresponding compounds wherein halogen is other than fluorine can be prepared by analogous methods.

Compounds of Formula I wherein A is —CH=CH— can be prepared from corresponding compounds wherein A is —$CH_2$—$CH_2$— by the method described by H. J. Reich, et al., J. Am. Chem. Soc., 1973, vol. 95, pp. 5813-5815. According to that method, a lithium enolate of an ester of Formula I (R=—$OR^3$) wherein one of $R^1$ and $R^2$ is other than hydrogen, is treated with phenylselenenyl bromide or chloride, and the resulting selenide is converted to the oxide, which undergoes elimination to form the olefinic compound. Suitable reagents for forming the enolates are lithium amides, such as lithium diisopropylamide, lithium cyclohexylisopropylamide and lithium bis(trimethylsilyl)amide (lithium hexamethyldisilazide). The conditions and techniques for carrying out the reactions are described in the Reich reference and are illustrated in specific instances in Examples 25 and 26, hereinafter. Compounds of Formula I wherein both $R^1$ and $R^2$ are hydrogen can be prepared by removing the substituent on the nitrogen atom, as is illustrated in Example 26.

Derivatives of the acids—i.e., esters and amides—can be prepared from the corresponding species of the acids by conventional methods, as described in U.S. Pat. No. 4,326,071, and demonstrated in particular instances in the examples set forth hereinafter.

Thus, the acids can be esterified, as shown inter alia in Examples 4, 5, 13 and 14 or converted to the amides, Examples 21 and 23. Preparation of compounds in which $R^2$ is a monovalent moiety is effected from the esters, Examples 6, 8, 13, or from the acids, Examples 10, 12 and 14. Preparation of the imines by condensation with an aldehyde or ketone ($R^1$ and $R^2$ forming the two bonds of the alkylidene linkage) is exemplified in Examples 18 and 20.

The examples described the preparation, isolation and physical properties of typical individual species of the compounds of Formula I, in particular instances.

In these examples, the identity of each product, and of any intermediate involved, was confirmed by appropriate chemical and spectral analyses.

EXAMPLES 1, 2 AND 3

Using the method of Silverman and Levy, J. Org. Chem., 45, 815-818 (1980), there were prepared:

(1) (S)-4-amino-5-chloropentanoic acid hydrochloride, (1), as a tan solid, m.p.: 133.5°-134.5° C.;

(2) (S)-4-amino-5-fluoropentanoic acid hydrochloride, (2), as a white solid, m.p.: 170°-171° C.; and (3) (S)-4-amino-5-bromopentanoic acid hydrobromide, (3), as a white solid, m.p.: 137°-138° C.

EXAMPLE 4

(S)-4-amino-5-fluoropentanoic acid methyl ester, hydrochloride (4)

5.15 g of 2 was added to 300 ml of dry methanol that had been saturated with hydrogen chloride, at 5°–10° C. The mixture was held at room temperature for 22 hours, then the methanol was evaporated under reduced pressure to give 4, as a heavy green oil.

EXAMPLE 5

(S)-4-amino-5-fluoropentanoic acid ethyl ester (5)

5 was prepared as a heavy pale yellow oil by the procedure described in Example 4, substituting an equivalent amount of ethanol for the methanol.

EXAMPLE 6

(S)-4-(acetylamino)-5-fluoropentanoic acid, methyl ester (6)

0.26 ml of triethylamine and 2 ml of glacial acetic acid were mixed with 0.34 g of 4. The mixture was cooled to 0° C. and 0.21 ml of acetic anhydride was added drop-by-drop to the stirred mixture. The mixture was allowed to warm to room temperature and stirred for 30 minutes. The solvents were evaporated under reduced pressure, the residue was triturated with a mixture of ethyl acetate and ether and filtered. The filtrate was eluted through a florisil pad, using ethyl acetate as eluent. The solvent was evaporated under reduced pressure to give 6, as a brown solid.

EXAMPLE 7

(S)-4-(acetylamino)-5-fluoropentanoic acid (7)

1.2 ml of 1N aqueous sodium hydroxide solution was added drop-by-drop to 0.22 g of 6 in 2 ml of methanol and the resulting mixture was stirred for one hour at room temperature. The methanol was evaporated, water and ethyl acetate were added to the residue, and the resulting mixture was acidified with a few drops of 12N hydrochloric acid. The mixture was stirred at room temperature for 30 minutes, the organic layer was separated, dried (Na$_2$SO$_4$), and stripped of solvent under reduced pressure. The residue, an oil, was triturated with ether/pentane to give 7, as a light brown powder, m.p.: 80°–83° C.

EXAMPLE 8

(S)-4-(trifluoroacetylamino)-5-fluoropentanoic acid, methyl ester (8)

0.28 g of triethylamine and 0.96 ml of trifluoroacetic acid were added to 0.28 g of 4, and the mixture was cooled to −10° C. 0.25 ml of trifluoroacetic anhydride was added drop-by-drop. The resulting mixture was allowed to warm to room temperature and stirred for 90 minutes. Volatile materials were evaporated under reduced pressure, and the residue, an oil, was eluted through a column of florisil, using ethyl acetate as eluent. After evaporation of the solvent, the resulting oil was stripped under reduced pressure to give 8, as a brown solid.

EXAMPLE 9

(S)-4-(trifluoroacetylamino)-5-fluoropentanoic acid (9)

9 was prepared, as an off-white solid, from 8 by the procedure described in Example 7.

EXAMPLE 10

(S)-4-((benzyloxycarbonyl)amino)-5-fluoropentanoic acid (10)

20 g of 2 was placed into 30 ml of 4N aqueous sodium hydroxide and the resulting mixture was cooled to 5° C. 18.4 ml of benzyl chloroformate and 40 ml of 4N aqueous sodium hydroxide solution were added, in portions alternately to the vigorously stirred mixture at 5° C., a basic pH being maintained throughout. The mixture was stirred for an additional 10 minutes, and then washed with an equal volume of ether. The aqueous phase was separated, acidified to pH 2 with concentrated hydrochloric acid, and extracted with ethyl acetate. The extract was dried (Na$_2$SO$_4$) and the solvent was evaporated under reduced pressure to give 10, as a white solid, m.p.: not determined.

EXAMPLE 11

(S)-4-((benzyloxycarbonyl)amino)-5-fluoropentanoic acid, cesium salt (11)

0.1 g of 10 was dissolved in 5 ml of methanol. Two drops of water were added, and then a 20% aqueous solution of cesium carbonate was added until the pH was 7 (0.4 ml). The solvents were evaporated under reduced pressure to give 11, as an off-white solid.

EXAMPLE 12

(S)-4-((ethoxycarbonyl)amino)-5-fluoropentanoic acid (12)

12 was prepared, as a pale yellow oil, by the procedure described in Example 10, substituting an equivalent amount of ethyl chloroformate for the benzyl chloroformate.

EXAMPLE 13

(S)-4-((benzyloxycarbonyl)amino)-5-fluoropentanoic acid, methyl ester (13)

A 20% aqueous solution of cesium carbonate was slowly added to a mixture of 14.2 g of 10 in 230 ml of methanol and 23 ml of water, until the mixture was neutral (about 50 ml of the carbonate solution). The solvent was evaporated under reduced pressure. The residue was placed in 50 ml of dimethylformamide and stripped twice. The residue was placed in 150 ml of dimethylformamide and 50 ml of methyl iodide was added to the mixture, which then was stirred overnight at room temperature. The mixture was filtered, and a large volume of methylene chloride was added to the filtrate. The filtrate was washed with a large volume of water, dried (Na$_2$SO$_4$) and the solvent was evaporated under reduced pressure. The residue was triturated with hexane, the mixture was filtered, and the solvent was evaporated from the filtrate to give 13, as a tan solid, m.p.: 46°–48° C.

EXAMPLE 14

(S)-4-((benzyloxycarbonyl)amino)-5-bromopentanoic acid (14)

14 was prepared as a colorless oil, by treatment of 3 with benzyl chloroformate, according to the procedure described in Example 10.

EXAMPLE 15

(S)-4-((benzyloxycarbonyl)amino)-5-chloropentanoic acid (15)

15 was prepared, as an amber oil, by treatment of 1 with benzyl chloroformate, according to the procedure described in Example 10.

EXAMPLE 16

(S)-4-((2,4-dichlorophenoxyacetyl)amino)-5-fluoropentanoic acid, methyl ester (16)

0.70 g of 2,4-dichlorophenoxyacetic acid, 0.59 g of 4 and 0.44 ml of trimethylamine were mixed with 75 ml of methylene chloride, and the mixture was stirred at room temperature for 30 minutes. Then, 0.65 g of N,N'-dicyclohexylcarbodiimide was added and the mixture was stirred at room temperature overnight. Several drops of glacial acetic acid were added and the mixture was filtered. The filtrate was washed successively with water, 1N hydrochloric acid, and half-saturated aqueous sodium bicarbonate solution, dried ($Na_2SO_4$) and stripped of solvent. The residue was triturated with ethyl acetate, the mixture was filtered and the solvent was evaporated from the filtrate under reduced pressure. The solid residue was triturated with hexane, the mixture was filtered and the solvent was evaporated from the filtrate. The solid residue was chromatographed over silica gel, first with a 1:3 v:v mixture of ethyl acetate and hexane as eluent, then with a 1:1 v:v mixture of ethyl acetate and hexane as eluent. On workup, 16 was obtained, as a white solid.

EXAMPLE 17

(S)-4-((2,4-dichlorophenoxyacetyl)amino)-5-fluoropentanoic acid (17)

0.77 ml of 1N aqueous sodium hydroxide solution was added to a stirred mixture of 0.27 g of 16 in 20 ml of methanol, the resulting mixture was stirred at reflux for one hour and then at room temperature over a weekend. The mixture then was filtered and the solvent evaporated from the filtrate. The residue was placed in water, ethyl acetate was added, then the mixture was acidified with 12N hydrochloric acid. The mixture was stirred for 30 minutes, then the organic phase was separated, dried ($Na_2SO_4$) and filtered. The solvent was evaporated from the filtrate to give a pale yellow oil. The oil was filtered through a florosil pad, eluted with ethyl acetate to give an oily solid, which was treated with methanol to give 17, as a white solid.

EXAMPLE 18

(S)-4-(5-Chlorosalicylideneamino)-5-fluoropentanoic acid (18)

0.50 g of 2 was dissolved in 83 ml of ethyl alcohol and 5.8 ml of methyl alcohol. Then 0.82 ml of triethylamine was added, followed by 0.46 g of 3-chloro-6-hydroxybenzaldehyde. The resulting mixture was stirred at room temperature overnight. The solvent was evaporated under reduced pressure. The solid residue was triturated with ether, the mixture was filtered and the solvent was evaporated from the filtrate to give 18, as a yellow oil.

EXAMPLE 19

(S)-4-((5-Chloro-2-hydroxybenzyl)amino)-5-fluoropentanoic acid (19)

0.42 g of 18 dissolved in a small amount of ethyl alcohol was added drop-by-drop to a mixture of 0.06 g of sodium borohydride, 3.6 ml of ethyl alcohol and 0.9 ml of water, at 10° C. The resulting solution was stirred and allowed to warm to room temperature overnight. The resulting mixture was quenched with water, and the resulting mixture was extracted with ethyl acetate. The extract was dried ($Na_2SO_4$), filtered and the solvent was evaporated to give 19, as an oily solid.

EXAMPLE 20

(S)-4-(2,6-dichlorobenzylideneamino)-5-fluoropentanoic acid, methyl ester (20)

0.36 g of 4 and 0.27 ml of triethylamine were mixed with 20 ml of benzene containing 0.5 g of 3A molecular sieve. 0.33 g of 2,6-dichlorobenzaldehyde was added and the mixture was stirred at room temperature overnight. 20 ml of ethyl acetate was added to the mixture, then it was filtered and the solvent was evaporated from the filtrate. The residue was dissolved in ethyl acetate, the solution was washed with saturated aqueous sodium bicarbonate solution, dried ($Na_2SO_4$) and the solvent was evaporated from the filtrate. The residue was thin layer chromatographed, using a 4:16:80 v:v:v mixture of tetrahydrofuran, ethyl acetate and hexane as eluent. Workup gave 20, as a yellow oil.

EXAMPLE 21

(S)-5-fluoro-4-((benzyloxycarbonyl)amino)pentanamide (21)

A solution of 2.65 g of thionyl chloride in 25 ml of methylene chloride was added drop-by-drop to a stirred solution of 6 g of 10 in 125 ml of methylene chloride, under nitrogen, at room temperature. After one hour of stirring, gaseous ammonia was bubbled into the mixture, at 23° C. to 10° C. (approximately 24.7 g of ammonia was charged). After two hours of further stirring, the resulting solution was diluted with methylene chloride, washed with water, dried ($Na_2SO_4$) and the solvent was evaporated from the filtrate. The residue was flash silica gel chromatographed, using a 1:9 v:v mixture of tetrahydrofuran and ethyl acetate as eluent. Two sets of fractions were collected, giving a yellow liquid and white solid. The solid was dissolved in ethyl acetate, about half of the solvent was evaporated and hexane was added to give a precipitate. The mixture was filtered, and the solid was dried to give 21, as a white solid, m.p.: 154.5°–157° C.

EXAMPLE 22

(S)-5-fluoro-4-aminopentanamide, hydrochloride salt (22)

0.46 g of 21 was hydrogenated in a Parr bottle, in methanol containing a small amount of concentrated hydrochloric acid and 10% palladium-on-carbon catalyst, at 32 p.s.i.g. hydrogen pressure for 6 hours at room temperature. The resulting mixture was filtered and the filtrate was stripped of solvent. The residue was triturated with ethyl acetate and the mixture was filtered to give 22, as a brownish solid, m.p.; 165°–175° C.

EXAMPLE 23

(S)-5-fluoro-N-(1-methylethyl)-4-((benzyloxycarbonyl)amino)pentamide (23)

A solution of 2.73 g of thionyl chloride in 25 ml of methylene chloride was added drop-by-drop to a stirred mixture of 6.16 g of 10 in 125 ml of methylene chloride, under nitrogen, at 25° C. The resulting mixture was stirred at 25° C. for an hour, then a solution of 2.70 g of isopropylamine in 5 ml of methylene chloride was added drop-by-drop, at 28° C. The resulting mixture was stirred for 1.5 hours, washed with water, and dried ($Na_2SO_4$), and the solvent was evaporated. The residue was flash chromatographed over silica gel, using a 1:1 v:v mixture of hexane and ethyl acetate as eluent, then with ethyl acetate as eluent. The solvent was evaporated from the second eluate, the residue was dissolved in ethyl acetate, about half of the ethyl acetate was evaporated, and hexane was added. The resulting solid was filtered from the mixture and dried to give 23, as a white solid, m.p.: 146°–148° C., which decomposed to a white solid, m.p.: 159°–161° C.

EXAMPLE 24

Methyl (S)-4-(benzoylamino)-5-fluoropentanoate (24)

1.0 ml of thionyl chloride was added drop-by-drop to a stirred mixture of 650 mg of 4 in 2.5 ml of methanol at room temperature. The resulting mixture was stirred at room temperature for 10 minutes, at reflux for two hours, cooled and stripped of solvent. The residue was mixed with 25 ml of chloroform and the mixture was stirred while 0.47 ml of benzoyl chloride was added drop-by-drop, then 1.2 ml of triethylamine was added, drop-by-drop. The mixture was stirred at room temperature for 16 hours, and the solvent was evaporated. The residue was mixed with 25 ml of water and the mixture was extracted with chloroform. The extract was washed successively with 1N hydrochloric acid, water, 1M sodium bicarbonate solution, and water. It then was dried ($MgSO_4$), the solvent was evaporated, and the residue was recrystallized from methylene chloride/hexane to give 24, as fine white needles, m.p.: 99.5°–100.5° C.

EXAMPLE 25

Methyl (S)-(E)-4-(benzoylamino)-5-fluoro-2-pentenoate (25)

A solution of 1.35 g of 24 in 60 ml of dry tetrahydrofuran was added drop-by-drop to a stirred solution of lithium cyclohexylisopropylamide (prepared from 2.3 ml of cyclohexylisopropylamine, 2.0 ml of tetramethylethylenediamine and 6.0 ml of a 2.2M solution of butyllithium in hexane) in 70 ml of dry tetrahydrofuran, at −78° C., under argon. The mixture was stirred at −78° C. for 45 minutes, then a solution of 1.1 g of phenylselenenyl chloride in 30 ml of dry tetrahydrofuran was added drop-by-drop. The mixture was stirred for 10 minutes at −78° C., then was warmed to −10° C. and poured into a mixture of 80 ml of 1N hydrochloric acid and 100 ml of ether. The ether phase was separated, washed successively with water, 5% hydrochloric acid, 5% sodium carbonate solution, and water, dried ($MgSO_4$) and stripped of solvent. The residue was dissolved in acetone at 0° C. and 4.3 ml of 30% hydrogen peroxide solution was added. The mixture was stirred at 0° C. for one hour, at room temperature for two hours, then the solvent was evaporated. The residue was diluted with 80 ml of water and the resulting mixture was extracted with ethyl acetate. The extract was washed with water, dried ($MgSO_4$), and the solvent was evaporated and the residue was recrystallized from ether/petroleum ether to give 25, as a pale yellow powder.

EXAMPLE 26

(S)-(E)-4-amino-5-fluoro-2-pentenoic acid (26)

A solution of 1.42 g of 13 in 25 ml of dry tetrahydrofuran was added drop-by-drop to a solution of lithium hexamethyldisilazide (prepared by adding 5.7 ml of a 2.2M solution of n-butyllithium in hexane drop-by-drop to a solution of 2.7 ml of hexamethyldisilazane and 1.9 ml of tetramethylethylenediamine in tetrahydrofuran) in 15 ml of dry tetrahydrofuran, at −78° C., under argon. The resulting solution was stirred for one hour at −78° C., then a solution of 0.96 g of phenylselenenyl chloride in 15 ml of dry tetrahydrofuran was added rapidly. The resulting solution was stirred at −78° C. for 10 minutes, warmed to −20° C. and quenched by the addition of 60 ml of 1N hydrochloric acid and 20 ml of cold water. The solution then was warmed to room temperature and extracted with ether. The extract was washed, successively, with water, 1N hydrochloric acid, 1N sodium bicarbonate solution and water. It then was dried ($MgSO_4$), the solvent was evaporated and the residue was chromatographed on silica gel, eluting first with n-hexane (to remove diphenylselenide) and then with 30% ethyl acetate/n-hexane to give, on work-up, methyl (S)-4-(benzyloxycarbonylamino)-5-fluoro-2-(phenylselenyl)pentanoate (26A), as a pale yellow oil.

4.2 ml of 30% hydrogen peroxide solution was added to a stirred solution of 1.4 g of 26A in 25 ml of acetone, at 0° C. The resulting solution was stirred at 0° C. for one hour, warmed to room temperature and the solvent was evaporated. The residue was diluted with 50 ml of cold water and 20 ml of 1N sodium bicarbonate solution and the resulting mixture was extracted with ethyl acetate. The extract was washed successively with water, 1N sodium bicarbonate solution and water, dried ($MgSO_4$) and the solvent was evaporated. The residue was chromatographed on silica gel, first eluting with n-hexane, then with 25% ethyl acetate/n-hexane, to give, on work-up, methyl (S)-(E)-4-(benzyloxycarbonylamino)-5-fluoro-2-pentenoate (26B), as a pale yellow viscous oil.

690 ml of 26B was stirred in 25 ml of trifluoroacetic acid at room temperature for 10 minutes. Then 5 ml of concentrated hydrochloric acid was added drop-by-drop. The resulting solution was stirred at room temperature for three hours, then 16 ml of water was added, and the resulting solution was stirred at room temperature for 16 hours. Then the solvent was evaporated, the residue was dissolved in 30 ml of 2N hydrochloric acid and the resulting solution was extracted with ether, and the solvent was evaporated at a temperature below 40° C. to give methyl (S)-(E)-4-amino-5-fluoro-2-pentenoate hydrochloride (26C), as a pale yellow paste.

410 mg of 26C was stirred in 25 ml of 5N hydrochloric acid for 48 hours at room temperature, then the solvent was evaporated at a temperature below 40° C. and the residue was dried over phosphorus pentoxide for 24 hours. The resulting product was recrystallized from acetic acid/ethyl acetate to give 26, as powdery white flakes, m.p.: 169°–170° C.

Compounds of Formula I have been found to affect adversely the growth of plants, and therefore to be useful for controlling the growth of unwanted plants.

Accordingly, the invention includes a method of combatting unwanted plants which comprises applying to the locus an effective amount of a compound of Formula I. For application, the compound generally is applied most effectively by formulating it with a suitable inert carrier or surface-active agent, or both. The invention, therefore, also includes compositions suitable for combatting unwanted plants, such compositions comprising an inert carrier or surface-active agent, or both, and as active ingredient at least one compound of Formula I.

The term "carrier" as used herein means an inert solid or fluid material, which may be inorganic or organic and of synthetic or natural origin, with which the active compound is mixed or formulated to facilitate its application to the plant, seed, soil or other object to be treated, or its storage, transport and/or handling. Any of the materials customarily employed in formulating pesticides, herbicides, or fungicides, are suitable.

Suitable solid carriers are natural and synthetic clays and silicates, for example, natural silicas such as diatomaceous earths; magnesium silicates, for example, talcs; magnesium aluminum silicates, for example, attapulgites and vermiculites; aluminum silicates, for example, kaolinites, montmorillonites and micas; calcium carbonate; calcium sulfate; synthetic hydrated silicon oxides and synthetic calcium or aluminum silicates; elements such as, for example, carbon and sulfur; natural and synthetic resins such as, for example, coumarone resins, polyvinyl chloride and styrene polymer s and copolymers; bitumen; waxes such as, for example, beeswax, paraffin wax, and chlorinated mineral waxes; solid fertilizers, for example, superphosphates; and ground, naturally-occurring, fibrous materials, such as ground corncobs.

Examples of suitable fluid carriers are water, alcohols such as, for example, isopropanol, glycols; ethers such as, for example, cellosolves; aromatic hydrocarbons such as, for example, benzene, toluene and xylene; petroleum fractions such as, for example, kerosene, light mineral oils; chlorinated hydrocarbons such as, for example, carbon tetrachloride, perchloroethylene, trichloroethane, including liquefied, normally vaporous, gaseous compounds. Mixtures of different liquids are often suitable.

The surface-active agent may be an emulsifying agent or a dispersing agent or a wetting agent; it may be non-ionic or ionic. Any of the surface-active agents usually applied in formulating herbicides or insecticides may be used. Examples of suitable surface-active agents are the sodium or calcium salts of polyacrylic acids and lignin sulfonic acids; the condensation products of fatty acids or aliphatic amines or amides containing at least 12 carbon atoms in the molecule with ethylene oxide and/or propylene oxide; fatty acid esters of glycerol, sorbitan, sucrose or pentaerythritol; condensates of these with ethylene oxide and/or propylene oxide; condensation products of fatty alcohols or alkyl phenols, for example, p-octylphenol or p-octylcresol, with ethylene oxide and/or propylene oxide; sulfates or sulfonates of these condensation products, alkali or alkaline earth metal salts, preferably sodium salts, or sulfuric or sulfonic acid esters containing at least 10 carbon atoms in the molecule, for example, sodium lauryl sulfate, sodium secondary alkyl sulfates, sodium salts of sulfonated castor oil, and sodium alkyl-aryl sulfonates such as sodium dodecylbenzene sulfonate; and polymers of ethylene oxide and copolymers of ethylene oxide and propylene oxides.

The compositions of the invention may be prepared as wettable powders, dusts, granules, solutions, emulsifiable concentrates, emulsions, suspension concentrates and aerosols. Wettable powders are usually compounded to contain 25, 50 or 75% by weight of the active compound and usually contain, in addition to the solid carrier, 3–10% by weight of a dispersing agent, 15% of a surface-active agent and, where necessary, 0–10% by weight of stabilizer(s) and/or other additives such as penetrants or stickers. Dusts are usually formulated as a dust concentrate having a similar composition to that of a wettable powder but without a dispersant or surface-active agent, and are diluted in the field with further solid carrier to give a composition usually containing 0.5–10% by weight of the active compound. Granules are usually prepared to have a size between 10 and 100 BS mesh (1.676–0.152 mm), and may be manufactured by agglomeration or impregnation techniques. Generally, granules will contain 0.5–25% by weight of the active compound, 0–1% by weight of additives such as stabilizers, slow release modifiers and binding agents. Emulsifiable concentrates usually contain, in addition to the solvent and, when necessary, cosolvent, 10–50% weight per volume of the active compound, 2–20% weight per volume emulsifiers and 0–20% weight per volume of appropriate additives such as stabilizers, penetrants and corrosion inhibitors. Suspension concentrates are compounded so as to obtain a stable, non-sedimenting, flowable product and usually contain 10–75% weight of the active compound, 0.5–5% weight of dispersing agents, 1–5% of surface-active agent, 0.1–10% weight of suspending agents, such as defoamers, corrosion inhibitors, stabilizers, penetrants and stickers, and as carrier, water or an organic liquid in which the active compound is substantially insoluble; certain organic solids or inorganic salts may be dissolved in the carrier to assist in preventing sedimentation or as antifreeze agents for water.

Aqueous dispersions and emulsions, for example, compositions obtained by diluting a wettable powder or a concentrate according to the invention with water, also lie within the scope of the present invention. The said emulsions may be of the water-in-oil or of the oil-in-water type, and may have a thick, mayonnaise-like consistency.

The compositions of the invention may also contain other ingredients, for example, other compounds possessing pesticidal, especially insecticidal, acaricidal, herbicidal or fungicidal properties, as are appropriate to the intended purpose.

Protection of a locus or area from undesirable plants is effected by applying a compound of Formula I, ordinarily in a composition of one of the aforementioned types, to soil in which the seeds of the unwanted plants are present, or to the foliage of the unwanted plants. The active compound, of course, is applied in an amount sufficient to exert the desired action.

The amount of the compound of the invention to be used in combatting undesired plants will naturally depend on the condition of the plants, the degree of activity desired, the formulation used, the mode of application, the climate, the season of the year, and other variables. Recommendations as to precise amounts are, therefore, not possible. In general, however, application to the locus to be protected of from 0.1 to 10.0 kg per hectare of the compound of Formula I will be satisfactory.

EXAMPLES OF ACTIVITY WITH RESPECT TO PLANTS

In the following examples, the species of plants that were tested were:
Barnyardgrass (watergrass)—*Enchinochloa crus-galli*
Large crabgrass—*Digitaria sanguinalis*
Downy brome—*Bromus tectorum*
Yellow foxtail—*Setaria lutescens*
Redroot pigweed—*Amaranthus retroflexus*
Sicklepod—*Cassia obtusifolia*
Velvetleaf *Abutilon theophrasti*
Garden cress—*Lepidium sativum*
Johnsongrass—*Sorghum halepense*

TEST PROCEDURES

The preemergence (soil) herbicidal activity of the compounds was evaluated by planting seeds of barnyardgrass, garden cress, downy brome, velvetleaf, yellow foxtail, and sicklepod in test tubes, nominally measuring 25×200 millimeters, filled about three-quarters full of untreated soil, in each case covered on top with about 2.5 cubic centimeters of soil treated with a certain amount of the test compound. The treated soil applied to the tubes containing the barnyardgrass and cress seeds contained one milligram of the test compound per tube, and contained 0.1 milligram of the test compound per each tube containing the seeds of the other plants. The dosages were approximately 20 and 2.0 pounds of test compound per acre, respectively. The seeds were planted on top of the treated soil and covered with about 1.5 cubic centimeters of untreated soil. The planted soil was held under controlled conditions of temperature, moisture, and light for 9 to 10 days. The amounts of germination and growth in each tube were evaluated on a 0 to 9 scale, the numeric ratings having the following meanings:

| Rating | Meaning |
| --- | --- |
| 9 | No living tissue |
| 8 | Plant severely damaged and expected to die |
| 7 | Plant badly damaged, but expected to live |
| 6 | Moderate damage, but complete recovery expected |
| 5 | Intermediate damage (probably unacceptable for crop plants) |
| 3-4 | Observable damage |
| 1-2 | Plant slightly affected, possibly by the chemical, possibly due to biological variability |
| 0 | No visible effect |

The postemergence (foliar) herbicidal activity of compounds of the invention was evaluated by spraying 10-day-old large downy brome plants in some cases, 6-day-old Johnsongrass plants in other cases, 9-day-old velvetleaf plants, 9-day-old yellow foxtail plants and 9-day-old sicklepod plants to runoff with a liquid formulation of the test compound. The crabgrass and pigweed plants were sprayed with 2.4 milliliters of a 0.25% solution (about ten pounds of the test compound per acre), and other plants were sprayed with 2.4 milliliters of a 0.025% solution (about one pound of the test compound per acre). The sprayed plants were held under controlled conditions of temperature, moisture and light for 7 to 8 days, and the effect of the test compound was then evaluated visually, the results being rated on the 0 to 9 scale described above.

Results of the preemergence and postemergence herbicidal activity tests are set forth in Table I.

TABLE I

| | HERBICIDAL ACTIVITY | | | | | | | | | | | |
| --- | --- | --- | --- | --- | --- | --- | --- | --- | --- | --- | --- | --- |
| | Preemergence | | | | | | Postemergence | | | | | |
| Compound | Barnyard-grass | Garden cress | Downy brome | Velvet-leaf | Yellow foxtail | Sickle-pod | Crab-grass | Pig-weed | Johnson-grass | Velvet-leaf | Yellow foxtail | Sickle-pod |
| 1 | 9 | 9 | 9 | 9 | 7 | 6 | 6 | 4 | 3 | 3 | 2 | 2 |
| 2 | 9 | 9 | 9 | 9 | 9 | 9 | 8 | 8 | 8 | 8 | 8 | 6 |
| 3 | 9 | 9 | 7 | 8 | 7 | 4 | 4 | 3 | 2 | 2 | 2 | — |
| 4 | 9 | 9 | 7 | 8 | 7 | 7 | 8 | 5 | 3 | 6 | 6 | 4 |
| 5 | 9 | 9 | 7 | 8 | 7 | 5 | 8 | 5 | 3 | 3 | 5 | 3 |
| 6 | 8 | 8 | 6 | 5 | 8 | 5 | 6 | 3 | 1 | 2 | 3 | 3 |
| 7 | 8 | 7 | 4 | 3 | 6 | 3 | 6 | 5 | 0 | 0 | 0 | 0 |
| 8 | 8 | 8 | 7 | 3 | 7 | 3 | 6 | 7 | 3 | 2 | 3 | 2 |
| 9 | 8 | 5 | 0 | 0 | 3 | 2 | 5 | 4 | 1 | 0 | 1 | 1 |
| 10 | 8 | 8 | 9 | 9 | 8 | 8 | 8 | 8 | 6 | 3 | 6 | 7 |
| 11 | — | — | 9 | 9 | 9 | 9 | — | — | 5 | 6 | 5 | 5 |
| 12 | 9 | 9 | 9 | 3 | 9 | 9 | 7 | 6 | 3 | 2 | 6 | 6 |
| 13 | 8 | 9 | 9 | 9 | 7 | 8 | 8 | 6 | 4 | 4 | 6 | 5 |
| 14 | 3 | 6 | 3 | 3 | 3 | 2 | 4 | 3 | 1 | 0 | 0 | — |
| 15 | 5 | 7 | 6 | 4 | 4 | 3 | 4 | 4 | 2 | 2 | — | 2 |
| 16 | 8 | 9 | 6 | 7 | 7 | 6 | 2 | 8 | 1 | 5 | 2 | 5 |
| 17 | 9 | 8 | 7 | 8 | 7 | 8 | 3 | 9 | 4 | 7 | — | 7 |
| 18 | 9 | 9 | 9 | 9 | 8 | 8 | 8 | 5 | 6 | 6 | 7 | 3 |
| 19 | 7 | 8 | 4 | 3 | 5 | 3 | 5 | 3 | 2 | 3 | 1 | 1 |
| 20 | 9 | 9 | 6 | 7 | 6 | 7 | 7 | 7 | 5 | 6 | 5 | 5 |
| 21 | 8 | 9 | 9 | 8 | 8 | 9 | 7 | 6 | 6 | 4 | 5 | 6 |
| 22 | 9 | 9 | 8 | 9 | 9 | 8 | 7 | 6 | 7 | 6 | 7 | 6 |
| 23 | 6 | 7 | 8 | 3 | 5 | 3 | 2 | 6 | 2 | 2 | 0 | 2 |
| 24 | 5 | 8 | 2 | 2 | 3 | 3 | 0 | 0 | 6 | 0 | 0 | 0 |
| 25 | 4 | 7 | 2 | 2 | 2 | 4 | 0 | 0 | 0 | 0 | 0 | 0 |
| 26 | 9 | 9 | 9 | 8 | 8 | 9 | 7 | 7 | 5 | 5 | 5 | 3 |

We claim:
1. A method for controlling the growth of unwanted plants at a locus which comprises applying to the locus an effective amount of a compound of the formula:

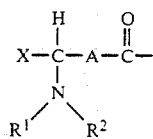

(I)

wherein X is (halogen)CH$_2$—, (halogen)$_2$CH—, or (halogen)$_3$C—; A is —CH$_2$—CH$_2$— or —CH=CH—; R is —OH, —OR$^3$, —NH$_2$ or —NHR$^3$, wherein R$^3$ is alkyl of one to six carbon atoms; R$^1$ is hydrogen, R$^2$ is hydrogen, —C(O)R$^4$, —C(O)OR$^4$ or —C(O)—CH$_2$—OR$^5$ wherein R$^4$ is alkyl of one to six carbon atoms optionally substituted by halogen, or is phenyl or benzyl optionally substituted by from one to three of one or more of halogen, nitro, hydroxyl and alkyl, alkoxy and alkylthio of from one to four carbon atoms, and R$^5$ is one of the phenyl moieties represented by R$^4$, or R$^1$ and R$^2$ together represent an alkylidene moiety

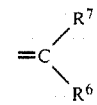

wherein R$^6$ is hydrogen and R$^7$ is a moiety represented by R$^4$, or R$^6$ and R$^7$ each is alkyl of from one to four carbon atoms, or is one of the phenyl moieties represented by R$^4$.

2. A method according to claim 1 wherein X is fluoromethyl, A is —CH$_2$—CH$_2$—, R is —OH, R$^1$ and R$^2$ each is hydrogen.

* * * * *